United States Patent
Arturo (10) Patent No.: US 6,749,430 B2
(45) Date of Patent: Jun. 15, 2004

(54) HEALING POST FOR INTRASURGICAL IMMOBILIZATION OF DENTAL IMPLANTS FOR IMMEDIATE LOADING

(76) Inventor: Hruska Arturo, Via Livigno 100-00188, Rome (IT)

( * ) Notice: Subject to any disclaimer, the term of this patent is extended or adjusted under 35 U.S.C. 154(b) by 115 days.

(21) Appl. No.: 10/013,244

(22) Filed: Dec. 10, 2001

(65) Prior Publication Data

US 2002/0072037 A1 Jun. 13, 2002

(30) Foreign Application Priority Data

Dec. 11, 2000 (IT) ..................................... RM2000A0652

(51) Int. Cl.⁷ ................................................ A61C 8/00
(52) U.S. Cl. ..................................................... 433/173
(58) Field of Search ................................ 433/172, 173, 433/174, 175, 176

(56) References Cited

U.S. PATENT DOCUMENTS

| 4,516,937 A | * | 5/1985 | Bosker | 433/173 |
| 5,082,442 A | * | 1/1992 | Rosen | 433/17 |
| 5,567,155 A | * | 10/1996 | Hansen | 433/172 |
| 5,993,213 A |  | 11/1999 | Schiel et al. | 433/173 |
| 6,257,890 B1 | * | 7/2001 | Khoury et al. | 433/173 |
| 6,312,259 B1 | * | 11/2001 | Kvarnstrom | 433/174 |

FOREIGN PATENT DOCUMENTS

EP 0 988 836 A3 1/2001

* cited by examiner

Primary Examiner—Cary E. O'Connor
(74) Attorney, Agent, or Firm—Gauthier & Connors, LLP (57) ABSTRACT

The present invention relates to a healing post for intrasurgical immobilisation of dental implant for immediate loading, comprising a body, a mechanism for fixing on an endo-osseus implant, a mechanism for orienteering with respect to the same endo-osseus implant, the body of the post providing a mechanism for the positioning and the locking of a stabilisation element between at least two contiguous posts.

14 Claims, 7 Drawing Sheets

HEALING POST FOR INTRASURGICAL IMMOBILIZATION OF DENTAL IMPLANTS FOR IMMEDIATE LOADING

The present invention relates to a healing post for intrasurgical immobilisation of dental implant for immediate loading.

More specifically, the invention concerns a post of the above kind allowing the immobilisation of more than one implant in such a way to avoid all the tangential loadings due to the tongue, to the lips and to the de-occlusion movements.

Still more specifically, the solution suggested according to the invention allows to the patient to immediately load the implant after the intervention.

As it is well known, in implantology, endo-osseus implants are used, of which many different solutions have been proposed in the specific technical field, that must be submerged within the bone and immobilised to allow its osteointegration, in order to be able to mount on the same the definitive prosthesis.

However, it is also known that to obtain such osteointegration it is necessary to wait some month (between 3 and 6 months).

Obviously, during this period, the patient is not able to freely use this "part" of the mouth. Not less important are for the patient the esthetical problems encountered all along the osteointegration period.

A used technique provides that the implant is osteointegrated completely covered under the gingiva, thus remaining immobilised, but also making a part of the mouth completely unusable.

Submersion of the implant has been the first immobilisation solution used, and it can be compared to a well realised orthopaedic cast.

In this situation, in order to in any case allow to the patient to temporarily use all the portions of the mouth, resin "provisional crowns" or "armoured" "provisional crowns" are mounted, for which it is in any case necessary to provide a locking, guaranteeing the immobilisation of the underlying implant.

A solution adopted provides the welding each other of two contiguous provisional crowns, that are provisionally cementified to the underlying implant. This solution is characterised by remarkable drawbacks, since often de-cementification or the breakage of the provisional capsule occurs, thus frustrating the immobilisation of the underlying implant, that is no yet osteointegrated. They are sufficient few hours to loose the implant.

In both cases, said technology required the use of a welding machine within the mouth of the patient, said step requiring the use of suitable welding machine.

In this situation, the Applicant suggests according to the present invention, a technical solution allowing to solve all the above mentioned problems, allowing the immobilisation of the implant, with the possibility of an immediate loading, and without the need of using a welding machine.

Therefore, main object of the present invention is that of providing a technical solution creating an immobilisation meso-structure, independent from the provisional crowns.

Another object of the present invention is that of providing a solution allowing to intra-surgically immobilise the implants to obtain an immediate loading.

The advantages for the patient obtained by the immobilisation allowing the immediate loading are well evident, and can be summarised in avoiding a second surgical intervention for the same patient, in avoiding to have a removable, provisional, prosthesis, for the whole healing period (it is well known how a provisional prosthesis moves and is not completely satisfactory under an esthetical and phonetic point of view). Further, remarkable are the psychological advantages for the patient.

It is therefore specific object of the present invention a healing post for intrasurgical immobilisation of dental implant for immediate loading, comprising a body, means for fixing on an endo-osseus implant, means for orienteering with respect to the same endo-osseus implant, said body of the post providing means for the positioning and the locking of a stabilisation element between at least two contiguous posts.

Preferably, according to the invention, said body of the post provides a vertical groove, wherein said stabilisation element inserts, the two lateral parts of said vertical groove being squashed by suitable tool in order to lock the stabilisation element.

Always according to the invention, said body of the post can be comprised of two parts, a first lower part, coupling with the endo-osseus implant and provided with vertical groove for housing the stabilisation element, and an upper part, couplable with said lower part, provided with a passage hole for said stabilisation element, and with means for blocking the stabilisation element.

Particularly, it is provided a vertical screw allowing to respectively block said two parts and at the same time to block the two parts of the post body.

Still according to the invention, said post body provides at least a horizontal hole, preferably two or more holes, for the insertion of the stabilisation element, the blocking of the stabilisation element being obtained by vertical screw screwed from above in said post body.

Further, according to the invention, said post body provides a vertical groove, partially threaded at the bottom, wherein said stabilisation element inserts, the blocking of said stabilisation element being obtained by a screw, screwed in said thread of the vertical groove.

Still according to the invention, said post body provides a horizontal groove, wherein said stabilisation element inserts, the blocking of said stabilisation element being obtained by a screw screwed in a vertical thread centrally obtained in said post body.

Furthermore, according to the invention, said post body provides two elastic arms, divided by a slot, and a lower seat, shaped and dimensioned in such a way to snapping block said stabilisation element.

Preferably, according to the invention, said stabilisation element is comprised of a bar, having a section, with suitable shape and dimension.

In a further embodiment of the post according to the invention, said post body provides a circumferential lateral groove, and said stabilisation element is comprised of a wire, winding about the post groove and about the groove of the adjacent one.

According to the invention, the post can be comprised of metal, particularly titanium of any grade, or titanium alloy.

Furthermore, according to the invention, said bar can be comprised of titanium, fibre glass, carbon fibre, or any other suitable material.

Furthermore, according to the invention, said post can have any suitable shape and sloping, according to the specific needings.

Further, according to the invention, said means for orienteering with respect to the same endo-osseus implant, can be polygonal, with three or more sides, or any other shape allowing the choose of the orientation between post and endo-osseus implant.

The present invention will be now described, for illustrative but not limitative purposes, according to its preferred embodiments, with particular reference to the figures of the enclosed drawings, wherein.

Making first reference to FIGS. 1–4, it is shown an embodiment of the healing post according to the invention, allowing an immediate loading of the implant.

Figure 1:
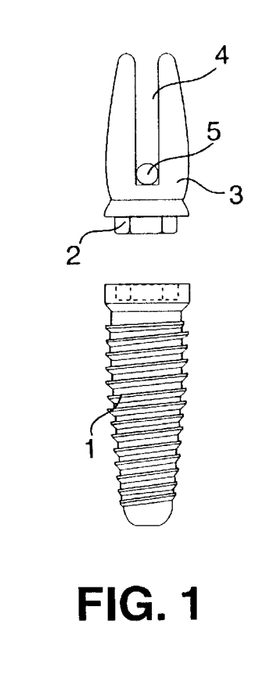
FIG. 1 is a lateral exploded view of a first healing post according to the invention, with the relevant implant.
Figure 2:
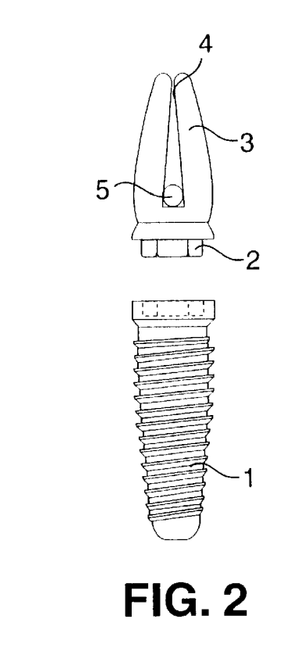
FIG. 2 is an exploded view of the post of FIG. 1, with the blocking of the stabilisation bar and the relevant implant.
Figure 3:
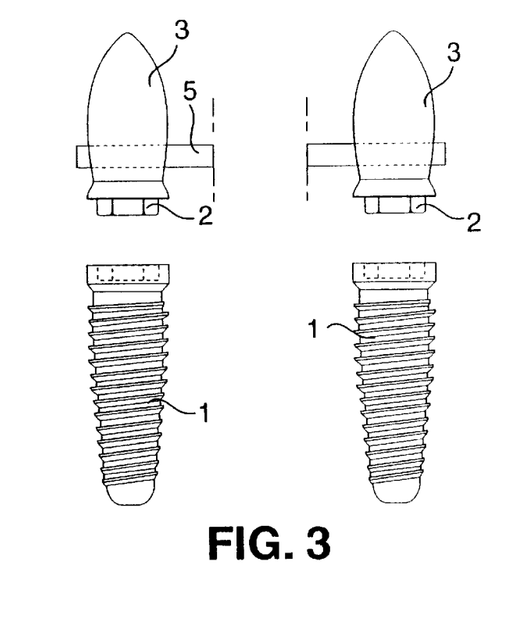
FIG. 3 is a front exploded view of two posts according to FIG. 1 with stabilisation bar and relevant implants.
Figure 4:
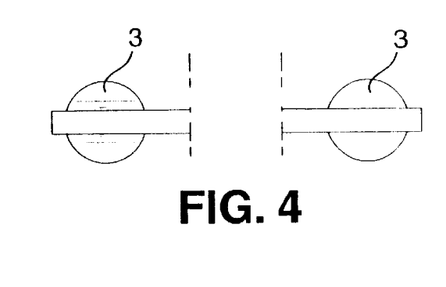
FIG. 4 is a top view of the two posts of FIG. 3.

Implant 1, of which in figure is shown one of the various possible solutions that can be employed with the post according to the invention, not being the kind of implant relevant for the successful use of the solution according to the present invention. In fact, the inventive solution can be used with any kind of existing implant, or that will be used in the future.

Further, it must be noted that the implants 1 presently available on the market have different positioning systems . In the figures shown, and particularly in FIGS. 1–4 and 6–21, it is shown a hexagonal positioning system 2 of the post 3 with respect to the implant 1, thus with six different positions, with the male element on the post 3 an the female element on the implant.

Figure 5:
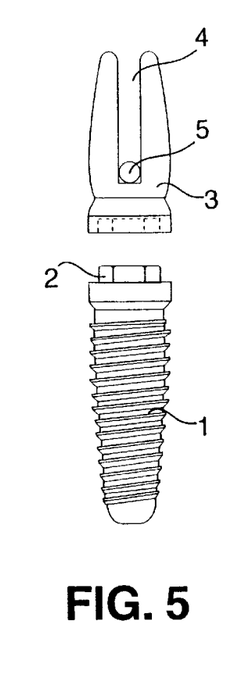
FIG. 5 is a lateral exploded view of the post of FIG. 1 with a different kind of positioning on the relevant implant.
Figure 6:
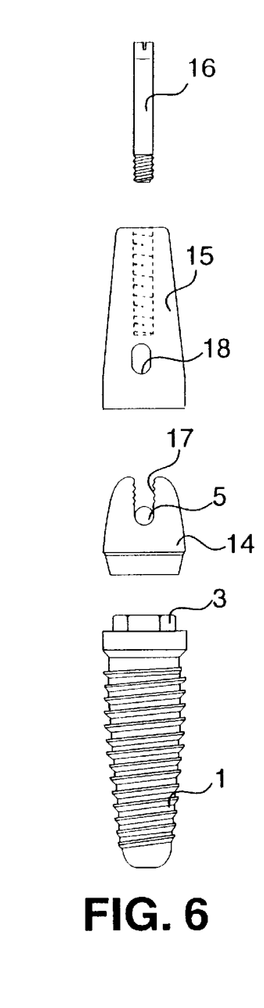
FIG. 6 is a lateral exploded view of a second healing post according to the invention, with the relevant implant.
Figure 7:
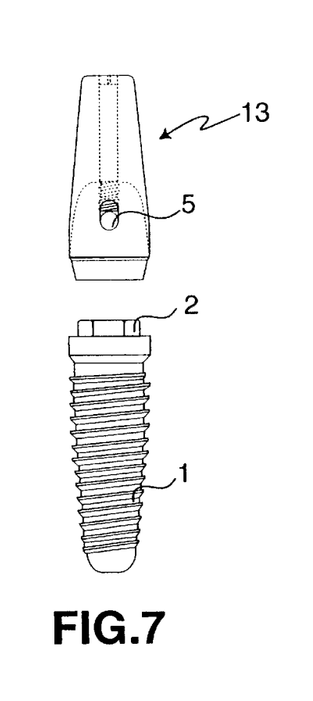
FIG. 7 is an exploded view of the post of FIG. 6, with the blocking of the stabilisation bar and the relevant implant.
Figure 8:
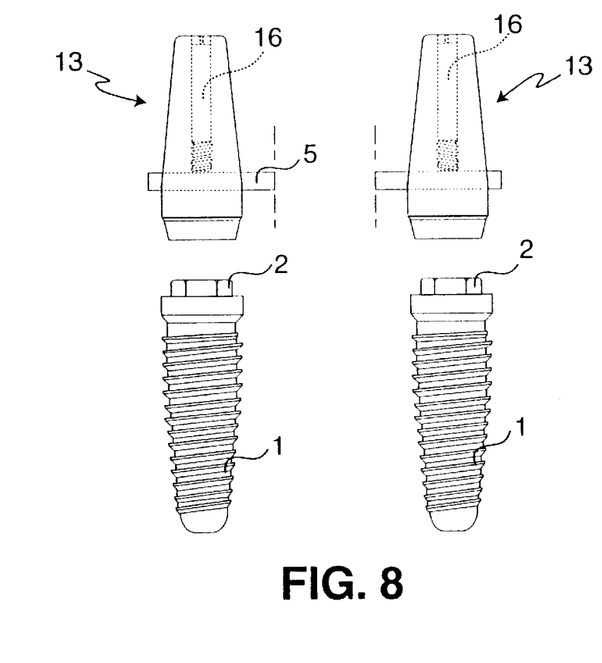
FIG. 8 is a front exploded view of two posts according to FIG. 6 with stabilisation bar and relevant implants.
Figure 9:
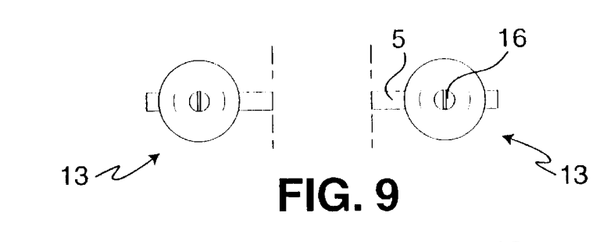
FIG. 9 is a top view of the two posts of FIG. 8.

In FIG. 5 it is shown a post 3 with implant 1, wherein the positioning system provides the male element on the implant 1 and the female element on the post 3.

Coming now to describe the solution shown in FIGS. 1–4, it is shown a first post 3 according to the invention, providing a slot 4, within which a stabilisation bar 5 is housed.

After the insertion of the implants 1, posts 3 are applied on the same implants, positioning the same with the proper orientation, by the system 2, and fixing them by a suitable screw, not shown, and thus the bar 5 is positioned between the two posts.

Thus, an action is carried out on the arms of the post 3, squashing by pliers or other suitable tool, thus blocking the stabilisation bar 5.

In this way, the immediate immobilisation of the same implant 1 is obtained.

Post of FIG. 5 is structurally identical to the one of the previous FIGS. 1–4, changing only the positioning system 5.

Coming now to observe FIGS. 6–9, it is shown a second embodiment of the healing post according to the invention, and the parts corresponding to those of the FIGS. 1–5 will be indicated by the same references.

In the solution shown, post 13 comprises a first part 14, coupling with the implant 1, by a little screw, not shown, and a second upper part 15, coupling with the lower part 14, by the screw 16, screwing within the thread 17 realised in the cavity 18 of the part 14 of the post 13.

Bar 5 is introduced within a hole 18, realised through the part 15 of the post 13. Blocking of the stabilisation bar 5 is obtained by the action of the same screw 16 coupling the two parts 14 and 15 of the post 13.

Figure 10:
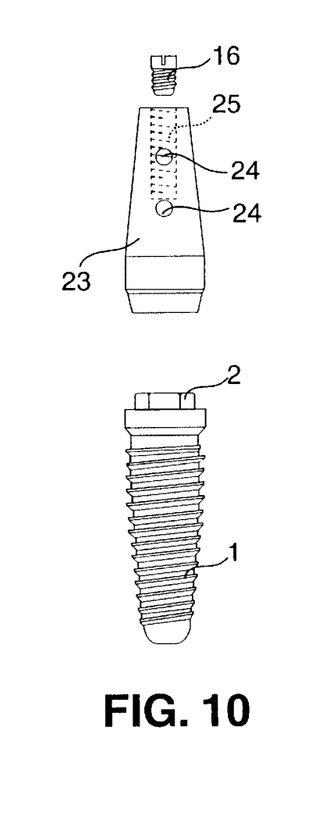
FIG. 10 is a lateral exploded view of a third healing post according to the invention, with the relevant implant.
Figure 11:
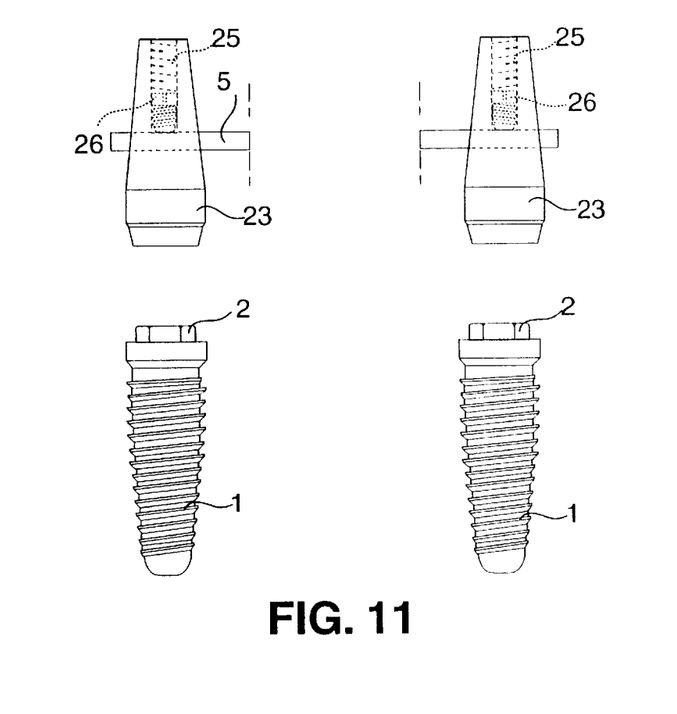
FIG. 11 is a front exploded view of two posts according to FIG. 10 with stabilisation bar and relevant implants.
Figure 12:
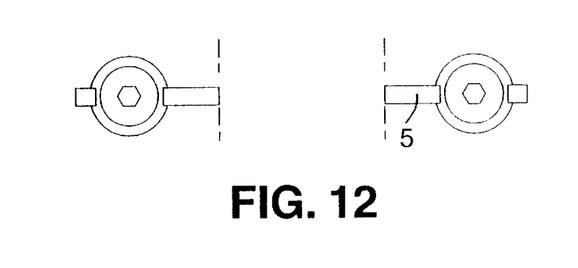
FIG. 12 is a top view of the two posts of FIG. 11.

Coming now to observe FIGS. 10–12, it is shown a third embodiment of the healing post according to the invention, and the parts corresponding to those of the FIGS. 1–5 will be indicated by the same references.

In the solution shown, post 23 comprises two holes 24 (obviously, the number of the holes 24 can be different, their number allowing to place the bar 5 according to the specific needings).

Bar 5 is introduced within one of the holes 24. Above the post 23, it is realised a thread 25, within which a little screw 26 is screwed, thus blocking the bar 5 in the proper position.

Figure 13:
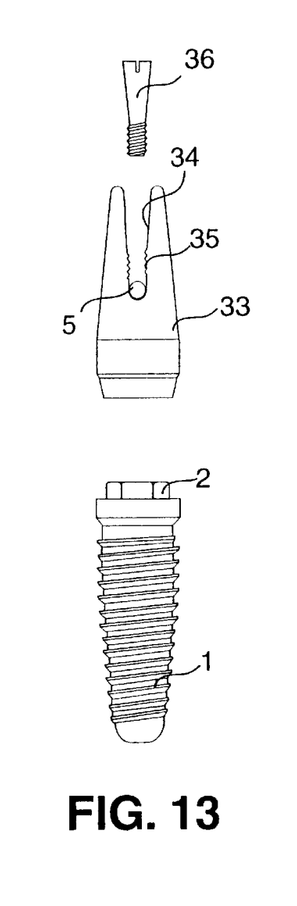
FIG. 13 is a lateral exploded view of a fourth healing post according to the invention, with the relevant implant.
Figure 14:
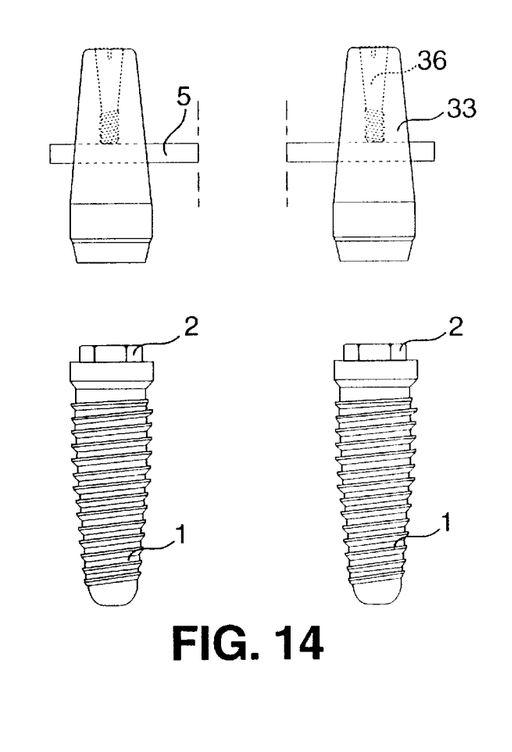
FIG. 14 is a front exploded view of two posts according to FIG. 13 with stabilisation bar and relevant implants.
Figure 15:
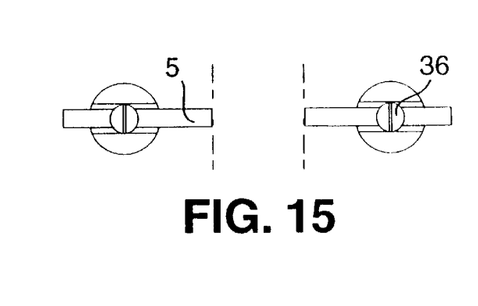
FIG. 15 is a top view of the two posts of FIG. 14.

Coming now to observe FIGS. 13–15, it is shown a fourth embodiment of the healing post according to the invention, and the parts corresponding to those of the FIGS. 1–5 will be indicated by the same references.

In the solution shown, post 33 comprises a slot 34, for the positioning of the bar 5, said slot being partially threaded 35 inside, to screw a little screw 36 blocking in the right position of the stabilisation bar 5.

Coming now to observe FIGS. 14–18, it is shown a fifth embodiment of the healing post according to the invention, and the parts corresponding to those of the FIGS. 1–5 will be indicated by the same references.

Figure 16:
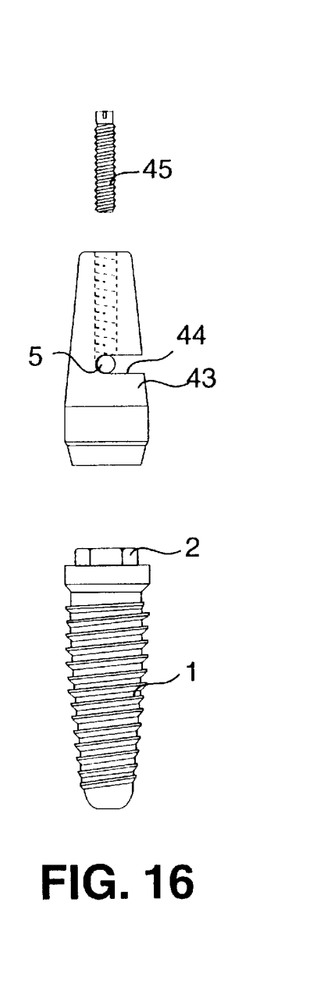
FIG. 16 is a lateral exploded view of a fifth healing post according to the invention, with the relevant implant.
Figures 17, 18:
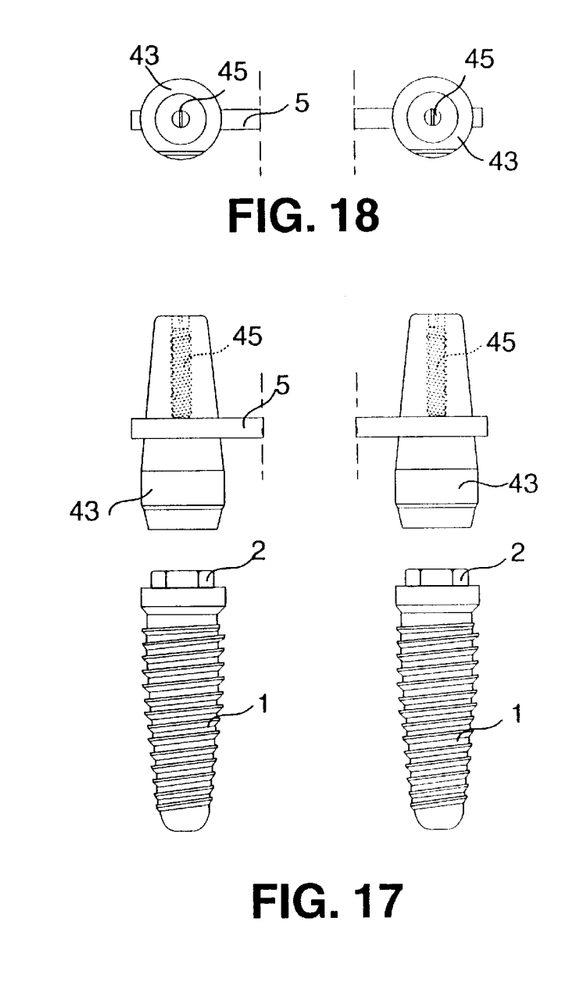
FIG. 17 is a front exploded view of two posts according to FIG. 16 with stabilisation bar and relevant implants.
FIG. 18 is a top view of the two posts of FIG. 17.

In the solution shown, post 43 comprises a lateral slot 44, wherein the stabilisation bar is laterally introduce.

Blocking of the bar into the post 43 occurs by a screw 45, screwing from above within the post 43.

Figure 19:
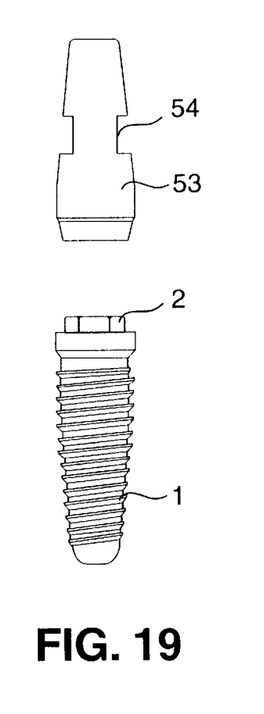
FIG. 19 is a lateral exploded view of a sixth healing post according to the invention, with the relevant implant.
Figure 20:
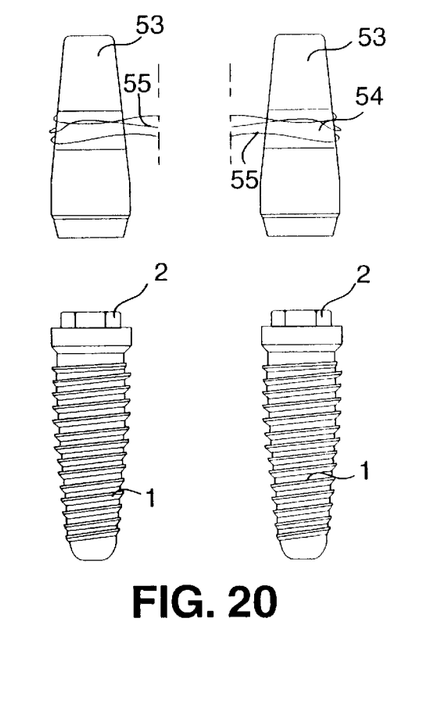
FIG. 20 is a front exploded view of two posts according to FIG. 19 with stabilisation bar and relevant implants.
Figure 21:
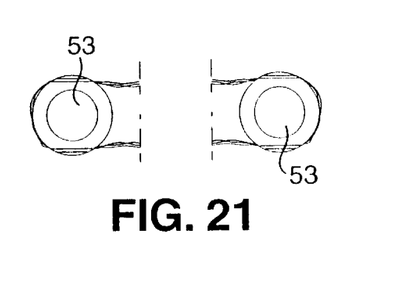
FIG. 21 is a top view of the two posts of FIG. 20.
Figure 22:
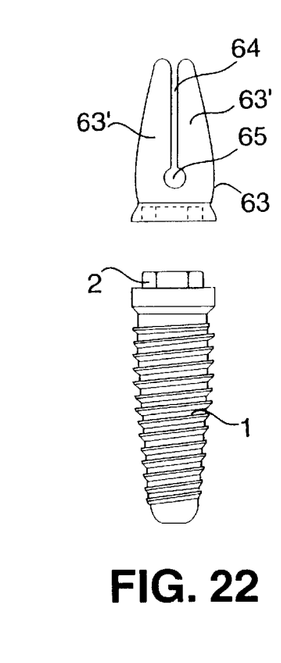
FIG. 22 is a lateral exploded view of a seventh healing post according to the invention, with the relevant implant.
Figure 23:
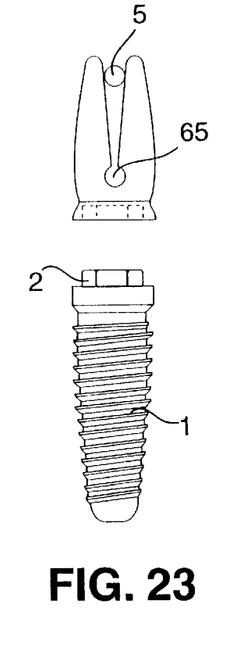
FIG. 23 is an exploded view of the post according to FIG. 22 with the insertion of the stabilisation bar and relevant implants.
Figure 24:
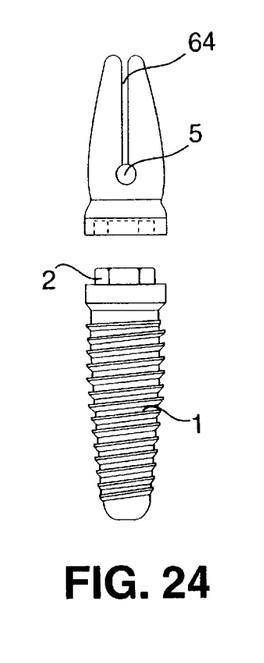
FIG. 24 is an exploded view of the two posts of FIG. 22 with the blocking of the stabilisation bar and relevant implant.
Figure 25:
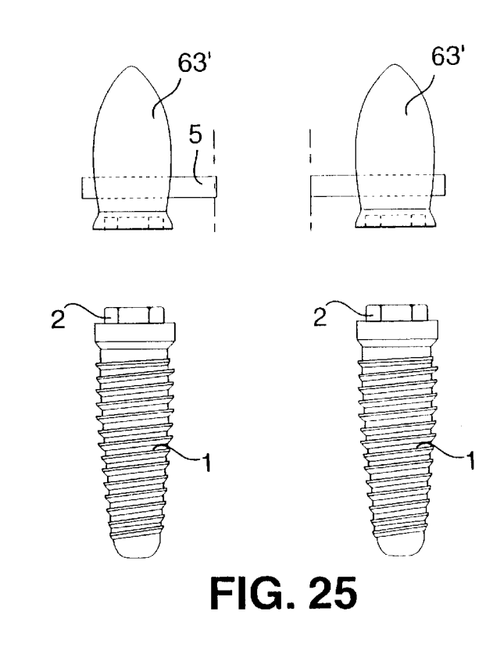
FIG. 25 is a front exploded view of two posts according to FIG. 22 with stabilisation bar and relevant implants; e
Figure 26:
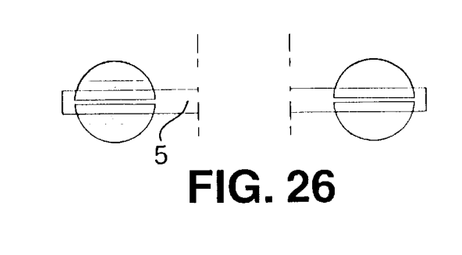
FIG. 26 is a top view of the two posts of FIG. 25.

Coming now to observe FIGS. 19–21, it is shown a sixth embodiment of the healing post according to the invention, and the parts corresponding to those of the FIGS. 1–5 will be indicated by the same references.

In the solution shown, post 53 provides a circumferential lateral slot 54, about which a suitable dental wire 55 is wound, in cooperation with the groove 54 of the adjacent post, said wire being provided with such physical properties to allow an easy use within the mouth and further to have a sufficient physical—structural resistance.

In all the various embodiments of the haling post according to the invention, the same post can be realised with any kind of suitable material or alloy, which is suitable to give an advantageous workability, a to guarantee the necessary resistance to the masticatory loading, that, as it is well known, are very high.

Coming now to describe the solution shown in FIGS. 22–26, it is shown a sixth post 63 according to the invention, providing two elastic arms 63', 63", separated by a slot 64, within which a stabilisation bar 5 is housed.

After the insertion of the implants 1, posts 63 are placed on the same implants, positioning them according to the proper orientation, by the system 2, and fixing them by a suitable screw, not shown.

Thus, the bar 5 is inserted, by an elastic forcing of the arms 63', 63", up to bring the same bar 5 to be fixed within the seat 65 realised at the bottom of the slot 64.

In this way, it is obtained the immediate immobilisation of the implant, so that the patient can immediately load the same implant.

After ostheosynthesis, bar 5 is cut, or removed, and thus the healing posts are unscrewed.

Osteointegrated implants are now ready for the traditional prosthetic rebuilding, exactly as occurs when a submerged implant is uncovered after the osteointegration.

After the osteointegration (3–4 months), the healing posts have to be removed and replaced with definitive traditional prosthetic ones.

The present invention has been described for illustrative but not limitative purposes, according to its preferred embodiments, but it is to be understood that modifications and/or changes can be introduced by those skilled in the art without departing from the relevant scope as defined in the enclosed claims.

What is claimed is:

1. A healing post for intrasurgical immobilization of a dental implant for immediate loading comprising a body, means for fixing on an endo-osseus implant, means for orienteering with respect to the same endo-osseus implant, said body of the post providing means for the positioning and the locking of a stabilization element between at least two contiguous posts, wherein said body of the post provides a vertical groove, such that said stabilization element is inserted, the two lateral parts of said vertical groove being squashed by suitable tool in order to lock the stabilisation element.

2. The healing post according to claim 1, wherein said stabilisation element is comprised of a bar, having a section, with suitable shape and dimension.

3. The healing post according to claim 1, wherein said post body provides a circumferential lateral groove, and said stabilisation element is comprised of a wire, winding about the post groove and about the groove of the adjacent one.

4. The healing post according to claim 1, wherein the post is comprised of metal.

5. The healing post according to claim 4, wherein the metal is titanium of any grade or titanium alloy.

6. The healing post according to claim 1, wherein said bar is comprised of titanium, fibre glass, carbon fibre, or any other suitable material.

7. The healing post according to claim 1, wherein said post has suitable shape and sloping, according to the specific needings.

8. The healing post according to claim 1, wherein said means for orienteering with respect to the same endo-osseus implant, is polygonal, with three or more sides, or any other shape allowing the choose of the orientation between post and endo-osseus implant.

9. The healing post according to claim 1, wherein said body of the post is comprised of two parts, a first lower part, coupling with the endo-osseus implant and provided with a vertical groove for housing the stabilization element, and an upper part, couplable with said lower part, provided with a passage hole for said stabilization element, and with means for blocking the stabilization element.

10. The healing post according to claim 1, wherein it is provided a vertical screw allowing to respectively block said two parts.

11. The healing post according to claim 1, wherein said post body provides at least a horizontal hole, for the insertion of the stabilization element, the blocking of the stabilization element being obtained by vertical screw screwed from above in said post body.

12. A healing post for intrasurgical immobilizatino of a dental implant for immediate loading comprising a body, means for fixing on an endo-osseus implant, means for orienteering with respect to the same endo-osseus implant, said body of the post providing means for the positioning and the locking of a stabilization element between at least two contiguous posts, wherein said post body provides a vertical groove, partially threaded at the bottom, wherein said stabilization element is inserted, the blocking of said stabilization element being obtained by a screw, screwed in said thread of the vertical groove.

13. A healing post for intrasurgical immobilization of a dental implant for immediate loading comprising a body, means for fixing on an endo-osseus implant, means for orienteering with respect to the same endo-osseus implant, said body of the post providing means for the positioning and the locking of a stabilization element between at least two contiguous posts, wherein said post body provides a horizontal groove, such that said stabilization element is inserted, the blocking of said stabilization element being obtained by a screw screwed in a vertical thread centrally obtained in said post body.

14. A healing post for intrasurgical immobilization of a dental implant for immediate loading comprising a body, means for fixing on an endo-osseus implant, means for orienteering with respect to the same endo-osseus implant, said body of the post providing means for the positioning and the locking of a stabilization element between at least two contiguous posts, wherein said post body provides two elastic arms, divided by a slot, and a lower seat, shaped and dimensioned in such a way to snap block said stabilization element.

* * * * *